United States Patent
Joly et al.

(10) Patent No.: US 9,442,073 B2
(45) Date of Patent: Sep. 13, 2016

(54) SENSOR COMPRISING A MASKING LAYER ADHESIVE

(75) Inventors: Guy D. Joly, Shoreview, MN (US); Duane D. Fansler, Dresser, WI (US); Neal A. Rakow, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 477 days.

(21) Appl. No.: 13/980,583

(22) PCT Filed: Mar. 5, 2012

(86) PCT No.: PCT/US2012/027652
§ 371 (c)(1),
(2), (4) Date: Jul. 19, 2013

(87) PCT Pub. No.: WO2012/134712
PCT Pub. Date: Oct. 4, 2012

(65) Prior Publication Data
US 2014/0007887 A1    Jan. 9, 2014

Related U.S. Application Data

(60) Provisional application No. 61/468,105, filed on Mar. 28, 2011.

(51) Int. Cl.
| G01N 33/52 | (2006.01) |
| G01N 31/22 | (2006.01) |
| G01N 21/75 | (2006.01) |
| G01N 21/78 | (2006.01) |
| A41D 13/11 | (2006.01) |
| B01D 46/00 | (2006.01) |
| G01N 21/77 | (2006.01) |

(52) U.S. Cl.
CPC ........... *G01N 21/78* (2013.01); *A41D 13/1161* (2013.01); *B01D 46/0086* (2013.01); *G01N 33/525* (2013.01); *G01N 2021/7779* (2013.01)

(58) Field of Classification Search
CPC ................................. C09J 133/12; C09J 4/00
USPC .................................................. 156/439, 524
See application file for complete search history.

(56) References Cited

U.S. PATENT DOCUMENTS

| 3,691,140 A | 9/1972 | Silver |
| 4,154,586 A | 5/1979 | Jones |
| 4,166,152 A | 8/1979 | Baker |

(Continued)

FOREIGN PATENT DOCUMENTS

| JP | 2005-313934 | 11/2005 |
| JP | 2010-506979 | 3/2010 |

(Continued)

OTHER PUBLICATIONS

Brandrup, "Polymer Handbook", pp. VI-209-VI-277, (1989).

(Continued)

*Primary Examiner* — Jill Warden
*Assistant Examiner* — Brittany Fisher
(74) *Attorney, Agent, or Firm* — Kent S. Kokko (57) ABSTRACT

Sensors (40) are described which comprise a reflective layer (52), a detection layer over the reflective layer (52), a semi-reflective layer (50) over the detection layer (48), and a masking layer (57) affixed to the reflective layer with a high Tg adhesive.

15 Claims, 1 Drawing Sheet

(56) References Cited

U.S. PATENT DOCUMENTS

| | | | |
|---|---|---|---|
| 4,326,514 A | 4/1982 | Eian | |
| 4,365,627 A | 12/1982 | Wing | |
| 4,530,706 A | 7/1985 | Jones | |
| 4,536,546 A * | 8/1985 | Briggs | C09J 4/06 |
| | | | 525/71 |
| 4,636,432 A | 1/1987 | Shibano | |
| 4,656,218 A | 4/1987 | Kinoshita | |
| 4,684,308 A | 8/1987 | Dorner | |
| 4,684,380 A | 8/1987 | Leichnitz | |
| 5,045,569 A | 9/1991 | Delgado | |
| 5,141,793 A * | 8/1992 | Fontanilla | B32B 27/06 |
| | | | 428/343 |
| 5,286,624 A | 2/1994 | Terashima | |
| 5,297,544 A * | 3/1994 | May | A62B 18/088 |
| | | | 128/202.22 |
| 5,323,774 A | 6/1994 | Fehlauer | |
| 5,858,457 A | 1/1999 | Brinker | |
| 6,010,751 A | 1/2000 | Shaw | |
| 6,180,318 B1 | 1/2001 | Fitzer | |
| 6,284,198 B1 | 9/2001 | Kirollous | |
| 6,396,616 B1 | 5/2002 | Fitzter | |
| 6,497,756 B1 | 12/2002 | Curado | |
| 6,573,305 B1 | 6/2003 | Thunhorst | |
| 7,442,237 B1 | 10/2008 | Gardner | |
| 7,449,146 B2 | 11/2008 | Rakow | |
| 7,690,514 B2 | 4/2010 | McKeown | |
| 8,225,782 B2 | 7/2012 | Rakow | |
| 8,336,543 B2 | 12/2012 | Holmquist-Brown | |
| 8,365,723 B2 | 2/2013 | Poirier | |
| 8,507,612 B2 | 8/2013 | Zhu | |
| 2002/0132111 A1* | 9/2002 | Zhou | C08K 5/3412 |
| | | | 428/343 |
| 2004/0184948 A1* | 9/2004 | Rakow | G01N 21/45 |
| | | | 422/1 |
| 2004/0223876 A1 | 11/2004 | Kirollos | |
| 2007/0137491 A1 | 6/2007 | Attar | |
| 2008/0063575 A1 | 3/2008 | Rakow | |
| 2008/0063874 A1* | 3/2008 | Rakow | C03C 17/38 |
| | | | 428/426 |
| 2008/0087196 A1 | 4/2008 | Anderson | |
| 2009/0163845 A1* | 6/2009 | Meyer-Ingold | A61L 15/24 |
| | | | 602/54 |
| 2009/0279168 A1* | 11/2009 | Hiwatashi | C09J 11/06 |
| | | | 359/359 |
| 2010/0189600 A1* | 7/2010 | Hulteen | G01N 21/783 |
| | | | 422/401 |
| 2010/0227969 A1 | 9/2010 | Zhu | |
| 2010/0233414 A1* | 9/2010 | Ishida | B32B 38/1808 |
| | | | 428/64.4 |
| 2011/0094514 A1 | 4/2011 | Rakow | |

FOREIGN PATENT DOCUMENTS

| | | |
|---|---|---|
| WO | 2005-111588 | 11/2005 |
| WO | 2010/075014 | 7/2010 |
| WO | 2010/135413 | 11/2010 |
| WO | 2010-135417 | 11/2010 |
| WO | 2011-123411 | 10/2011 |

OTHER PUBLICATIONS

Budd, "Free Volume and intrinsic microporosity in polymers", Journal of Materials Chemistry, 2005, vol. 15, pp. 1977-1986.

Budd, "Polymers of Intrinsic Microporosity (PIMs): Robust, Solution-Processable, Organic Microporous Materials," Chem. Commun., 2004, pp. 230-231.

Budd, "Solution-Processed, Organophilic Membrane Derived from a Polymer of Intrinsic Microporosity", Advanced Materials, Mar. 2004, vol. 16, No. 5, pp. 456-459.

Jia, "Synthesis of Microporous Silica Templated by Gelatin", Chemistry Letters, 2004, vol. 33, No. 2, pp. 202-203.

Krause, "Bicontinuous Nanoporous Polymers by Carbon Dioxide Foaming", Macromolecules, Nov. 1, 2001, vol. 34, No. 25, pp. 8792-8801.

Kresge, "Ordered mesoporous molecular sieves synthesized by a liqid-crystal template mechanism", Nature, Oct., 1992, vol. 359, pp. 710-712.

McKeown, "Polymers of Intrinsic Microporosity (PIMs): Bridging the Void between Microporous and Polymeric Materials," Chem. Eur. J., 2005, vol. 11, No. 9, pp. 2610-2620.

Ogawa, "A Simple sol-gel route for the preparation of silica-surfactant mesostructured materials", Chem. Commun., 1996, pp. 1149-1150.

Sorenson, "Preparative Methods of Polymer Chemistry", Interscience Publishers, New York, pp. 208-210, (1968).

Walheim, "Nanophase-Separated Polymer Films as High-Performance Antireflection Coatings", Science, 1999, vol. 283, No. 5401, pp. 520-522.

International Search Report for PCT International Application No. PCT/US2012/027652, mailed on Jul. 2, 2012, 5 pages.

* cited by examiner

US 9,442,073 B2

SENSOR COMPRISING A MASKING LAYER ADHESIVE

CROSS REFERENCE TO RELATED APPLICATIONS

This application is a national stage filing under 35 U.S.C. 371 of PCT/US2012/027652, filed Mar. 5, 2012, which claims priority to Provisional Application No. 61/468,105, filed Mar. 28, 2011, the disclosure of which is incorporated by reference in its/their entirety herein.

TECHNICAL FIELD OF THE INVENTION

This disclosure relates to colorimetric sensor films.

BACKGROUND OF THE INVENTION

The development of robust chemical sensors for a range of analytes remains an important endeavor for applications such as environmental monitoring, product quality control, and chemical dosimetry. Among the many methods available for chemical sensing, colorimetric techniques remain advantageous in that the human eye can be used for signal transduction, rather than extensive instrumentation.

Though colorimetric sensors currently exist for a range of analytes, most are based upon employing dyes or colored chemical indicators for detection. Such compounds are typically selective, meaning arrays are necessary to enable detection of various classes of compounds. Moreover, many of these systems have lifetime limitation issues, due to photo-bleaching or undesirable side reactions. Other optical sensing techniques, such as surface plasmon resonance and spectral interferometry, require substantial signal transduction hardware to provide response, and thus are not useful for simple visual indication.

Sensors are commonly used to detect the presence or absence of a particular chemical. Known sensors have been provided in a variety of forms for achieving this purpose. For example, signs and badges have been developed—see, for example, U.S. Pat. No. 6,284,198 and U.S. Patent Application 2004/0223876A1—along with filters, filter cartridges, and breathing masks (respirators) that include chemical indicators—see, for example, U.S. Pat. Nos. 5,323,774, 5,297,544, and 4,684,308. One particular chemical sensor that has been developed is a passive end-of-service-life indicator (ESLI) that has a film-like body. Within the film body is a detection layer that detects the presence of a particular chemical. Examples of film-like passive ESLIs are described in U.S. Patent Publications 2008/0063575A1 and 2008/0063874A1 to Rakow et al. ESLIs may be tailored to respond to various organic vapors and reactive gases.

ESLIs have been used in filter cartridges to assist in informing the user of when the cartridge has met the end of its service life—see, for example, U.S. Pat. Nos. 7,442,237, 6,497,756, 5,323,774, 5,297,544, 4,684,380, 4,530,706, 4,365,627, 4,326,514, 8,336,543, 8,225,782, 8,365,723, 7,503,962 and 4,154,586. The ESLIs are disposed adjacent to the housing sidewall so that they can be easily viewed from the exterior. The ESLIs are generally designed to be colorimetric sensors that is they change color after being exposed to a sufficient amount of contaminant in the filtered air. The color change and sensor placement are tailored to provide indication that coincides with when the filter cartridge service life ends. One particular problem with colorimetric ESLIs is that the wearer needs to observe the ESLI normal to the plane of the device to avoid reduction in contrast. With a reduction is contrast between exposed and unexposed areas of the ESLI, incorrect reading may be obtained.

SUMMARY OF THE INVENTION

The present invention features novel multilayered sensors. The sensors typically constitute a multi-layered interference filter whose hue shifts upon analyte exposure. The multilayered structure provides a versatile platform for incorporating a variety of chemistries that can detect a range of species. The films are flexible and robust, and can be designed to provide fast, reversible (or, in some cases, permanent) responses.

The sensors of the present invention may comprise a reflective layer, a detection layer over the reflective layer, and a semi-reflective layer over the detection layer. More specifically the present disclosure provides a chemical sensor comprising:
a) a multilayer body comprising:
  i) a semireflective layer;
  ii) a detection layer that undergoes a visual change in response to the presence of a chemical agent;
  iii) a reflective layer; and
b) an adhesive masking layer affixed to the surface of the reflective layer, said adhesive masking layer comprising an adhesive (meth)acryloyl copolymer having a $T_g$ of $\geq 0°$ C., and comprising a) high $T_g$ monomer units and b) alkyl (meth)acryloyl monomer units.

The adhesive masking layer precludes a portion of the detection layer from undergoing a visual change in response to a chemical agent. Thus the masking layer provides an internal contrast in the sensor where a portion of the detection layer undergoes a visual change, and the portion of the sensor where the adhesive masking layer is affixed does not undergo a visual change.

It has been found that the nature of the adhesive of the adhesive masking layer affects the performance of the sensor. With many adhesives, the contrast is diminished between the exposed regions of the sensor and those masked by the adhesive masking layer, particularly at acute viewing angles. That is the contrast between the exposed and masked regions may be less distinct when viewed at angles less than 90° relative to the plane of the sensor.

Additional layers may also be present in the sensors as long as the additional layers do not negatively impact the ability of the sensor to detect a given analyte. When present, additional layers may be present between any of the above-mentioned layers (i.e., the reflective layer, the detection layer, and the semi-reflective layer) and/or on either side of the reflective layer and/or the semi-reflective layer.

A variety of layer configurations and materials may be used to form the colorimetric sensors of the present invention. For example, the reflective layer of the colorimetric sensor may be a substantially continuous layer or a discontinuous layer, and may comprise one or more individual layers. The detection layer may comprise a single or multiple layers containing (i) at least one polymer component, (ii) at least one inorganic component, or (iii) a combination of (i) and (ii). In addition, like the reflective layer, the semi-reflective layer may be a substantially continuous layer or a discontinuous layer, and may comprise one or more individual layers. The construction and composition of the colorimetric sensors of the present invention will vary depending on a number of factors including, but not limited to, the analyte or analytes of interest, the medium containing the analyte or analytes, and the desired sensitivity of the sensor.

In one exemplary embodiment, the present invention is directed to a colorimetric sensor for measuring one or both of the presence and concentration of an analyte comprising a substantially continuous reflective layer; a detection layer over the reflective layer, the detection layer comprising at least one polymer component, said detection layer being capable of a change in optical thickness upon exposure to said analyte; and a substantially continuous semi-reflective layer over the detection layer, the semi-reflective layer having an index of refraction different from the index of refraction of the detection layer, wherein at least a portion of the reflective layer is permeable to said analyte.

In a further exemplary embodiment, the present invention is directed to a colorimetric sensor for measuring one or both of the presence and concentration of an analyte comprising a substantially continuous reflective layer; a detection layer over the reflective layer, the detection layer comprising at least one polymer component; and a substantially continuous semi-reflective layer over the detection layer, the semi-reflective layer having an index of refraction different from the index of refraction of the detection layer, said sensor being capable of a change in color upon exposure to said analyte.

In yet a further exemplary embodiment, the present invention is directed to a colorimetric sensor for measuring one or both of the presence and concentration of an analyte, wherein the colorimetric sensor comprises a substantially continuous reflective layer; a detection layer over the reflective layer, the detection layer comprising (i) at least one polymer component, (ii) at least one inorganic component, or (iii) both (i) and (ii); and a substantially continuous semi-reflective layer over the detection layer, the semi-reflective layer having an index of refraction different from the index of refraction of the detection layer and being permeable to said analyte, said sensor being capable of a change in color upon exposure to said analyte.

In even a further exemplary embodiment, the present invention is directed to a colorimetric sensor for measuring one or both of the presence and concentration of an analyte, wherein the colorimetric sensor comprises a reflective layer; a detection layer over the reflective layer; and a discontinuous semi-reflective layer over the detection layer, the semi-reflective layer having an index of refraction different from the index of refraction of the detection layer, said sensor being capable of a change in color upon exposure to said analyte. In this embodiment, the sensor desirably has at least one of the following features: (a) the discontinuous semi-reflective layer comprises a single layer of semi-reflective islands having at least one dimension greater than 10 μm, and exposed areas between the semi-reflective islands, said exposed areas having a width of at least 1.0 μm; (b) the discontinuous semi-reflective layer comprises a single layer of semi-reflective islands and the detection layer contains wells extending a depth into the detection layer; (c) the discontinuous semi-reflective layer comprises a single layer of semi-reflective islands and the detection layer comprises at least one inorganic component either alone or in combination with at least one polymer component; (d) the detection layer comprises at least one inorganic component, wherein said at least one inorganic component is (i) blended with at least one polymer component, (ii) within a given layer containing at least one polymer component but not blended with the at least one polymer component, (iii) in a layer separate from a layer containing at least one polymer component, or (iv) any combination of (i) to (iii); and (e) the detection layer comprises at least two different polymeric components, wherein the polymeric components are (1) blended with one another, (2) within a given layer but not blended with one another, (3) in a layer separate from one another, or (4) any combination of (1) to (3).

The present invention is further directed to arrays of sensors. One or more similar or different colorimetric sensors of the present invention may be combined to form an array of sensors capable of providing a composite signal to a user upon exposure to one or more analytes. Such composite signals can provide additional information, such as the identity of a pure analyte or a mixture of analytes, relative to a signal produced by a single colorimetric sensor.

The present invention is even further directed to a device comprising a colorimetric sensor and a light source, a housing component, or a combination thereof.

The present invention is also directed to a method of detecting the presence or absence of an analyte comprising providing a colorimetric sensor (or array of sensors) as described above, providing a light source, contacting the sensor (or array of sensors) with a medium that may contain an analyte, and monitoring the sensor (or array of sensors) for a change in optical properties.

As used in this invention:

"analyte" means the specific component that is being detected in a chemical or biochemical analysis, such as a chemical agent;

"dimensional change" means a change of distance in a direction normal to the surface of the detection layer surface;

"porous material" means a material containing a continuous network of pores throughout its volume;

"reflective" means semi-reflective or fully reflective;

"semi-reflective" means neither fully reflective nor fully transmissive, preferably about 30 to about 70% reflective, more preferably about 40 to about 60% reflective.

"substantially continuous" means a layer of material is non-porous, but may have cracks, grain boundaries, or other structures that create pathways through the layer of material. A "substantially continuous" layer may be non-porous, but permeable to one or more analytes.

"discontinuous" means a layer of material having at least two separate and distinct islands with empty space therebetween, wherein the at least two separate and distinct islands with empty space therebetween are within a given plane.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

DETAILED DESCRIPTION

Figure 1:
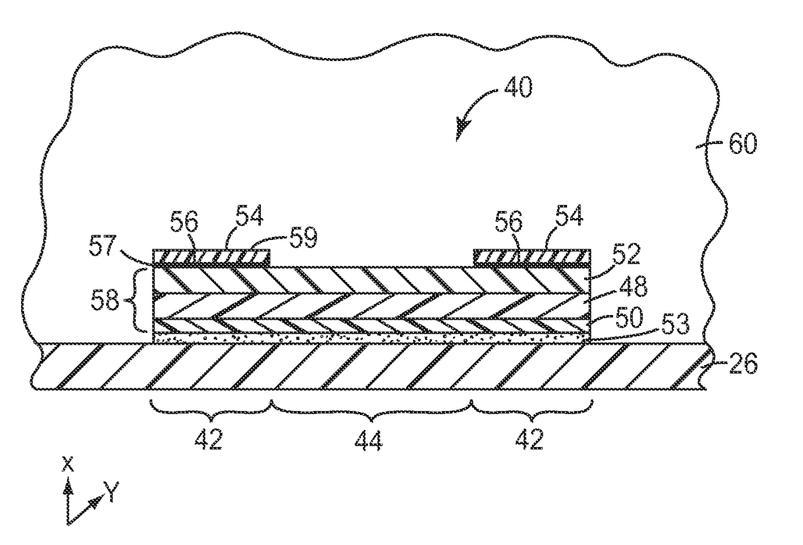
FIG. 1 is a cross-section of a sensor of the invention.

The present disclosure provides a chemical sensor comprising:
a) a multilayer body comprising:
  i) a semireflective layer;
  ii) a detection layer that undergoes a visual change in response to the presence of a chemical agent;
  iii) a reflective layer; and
b) an adhesive masking layer affixed to the surface of the reflective layer, As shown in FIG. 1, the sensor 40 may comprise a thin film multilayer construction that can detect a chemical agent in contact with the sensor, such a flowing from the gas inlet to the gas outlet of a respirator filter cartridge. Such passive sensors typically have a multilayer body that contains a porous detection layer 48, a semi-reflective layer 50, and a reflective layer 52. The porous detection layer 48 has an optical thickness (physical thickness does not necessarily change) that will change in the presence of a particular chemical. The semi-reflective layer 50 is viewable and is generally not permeated by the vapor. The reflective layer 52 is generally permeable to the chemical agent such that the chemical agent (such as a vapor) can pass through the reflective layer into the detection layer 48 and can change the detection layer optical thickness sufficiently to cause a visibly discernible change in the indicator appearance as viewed through the semi-reflective layer 50. An optional adhesive 53 may be used to secure the sensor 40 to optional substrate 26, which may be a portion of a respirator filter cartridge.

An adhesive masking layer, which comprises optional masking film 54 and adhesive (meth)acryloyl adhesive copolymer 57 may be disposed on opposing sides of the second region 44, which region 44 changes visually, such as a perceived color change, in response to exposure to one or more chemical agents. The masking layer may be bonded to the reflective layer 52 at an interface 56 with an adhesive (meth)acryloyl copolymer 57. The masking layer may be an adhesive (meth)acryloyl copolymer 57 per se, but preferably includes masking film layer 54. The masking layer is inert to the detection layer 48, i.e. areas masked by the masking layer do not under a visual change in response to a chemical agent.

When the masking layer 54 and 57 is bonded to the reflective layers 52, the detection layer 48 does not undergo a substantial optical change in regions 42. Without a masking layer 54 and 57 bonded to the film body 58, the film body 58 would normally produce a visual change, such as a color change, to a person viewing the film body normal to the outer major surface of the sensor 40. Thus, when the film is viewed in the direction x normal to the first major surface 59 of the masking layer 54, no visible change is seen in regions 42 of the sensor. The first region 42 therefore does not change visually, whereas the second region 44, exposed to the chemical agent, produces a noticeable change that is visible to a user viewing the sensor 40 in the direction x. Although regions 42 and 44 display different colors or hues, the regions are integral to each other in the film body 58. When a chemical is passing through the filter media 60, a progressive color change may be noticed by the user moving from the upstream side of the filter media towards the downstream side.

It has been discovered that when sensor 40 is observed from angles other than "x", such as acute angle "y", the contrast between regions 42 and 44 is diminished. With many adhesives of adhesive layer 57, this diminished contrast can lead to false readings. However with the adhesive (meth)acryloyl copolymer used in layer 57, the contrast is retained A sensor that is used in connection with the present invention may be rigid or flexible. It can be secured to the optional substrate 26 by various means such as adhesive 53 or by other means such as packing techniques, or mechanical engagement. Flexible indicators desirably are sufficiently bendable without fracturing so that they can be made using one or more roll processing steps.

Semi-Reflective Layer

The semi-reflective layer may comprise any material that can form a semi-reflective layer and has a different index of refraction than the detection layer. Desired thicknesses will depend on the material used to form the layer, the analyte to be detected, and the medium that will carry the analyte.

Suitable materials include metals and semi-metals such as aluminum, chromium, gold, nickel, silicon, and silver. Other suitable materials that may be included in the semi-reflective layer include oxides such as aluminum oxide, titanium oxide, and chromium oxide. The semireflective layer includes constructions of metal layers deposited on transparent films, such as vapor deposited nickel on polyethylene terephthalate films.

Like the reflective layer, the semi-reflective layer may be a substantially continuous layer or a discontinuous layer. Further, like the reflective layer, the semi-reflective layer may comprise one or more semi-reflective layers. Desirably, the semi-reflective layer comprises a single semi-reflective layer, which is either substantially continuous or discontinuous.

In one exemplary embodiment, the semi-reflective layer is a substantially continuous layer. In this embodiment, the construction and composition of the semi-reflective layer may be substantially consistent across an upper surface of and throughout the semi-reflective layer. Alternatively, the construction and/or composition of the semi-reflective layer may vary across an upper surface of and throughout the semi-reflective layer. For example, the semi-reflective layer may have a differential permeability such that the semi-reflective layer has higher analyte permeability for a given analyte at a first location on an upper surface of the semi-reflective layer and lower analyte permeability for the same analyte at a second location on the upper surface. The first and second locations on the upper surface of the semi-reflective layer may be randomly positioned relative to one another, or may form a pattern on the upper surface.

The substantially continuous semi-reflective layer may also have a pattern therein wherein first regions of the semi-reflective layer have a greater light reflectance than second regions of the semi-reflective layer. The first and second regions on the semi-reflective layer may form a pattern on the upper surface of and within the semi-reflective layer. Like the patterned detection layer described above, a patterned semi-reflective layer may comprise a pattern so as to create colored images, words, or messages upon exposure of the underlying detection layer to an analyte. The semi-reflective layer can provide easily identifiable warnings for a user upon exposure to an analyte.

Any number of methods may be used to alter the permeability of the semi-reflective layer and/or create a pattern on and within the semi-reflective layer. Suitable methods include, but are not limited to, spatially controlling the deposition conditions of the semi-reflective layer to vary the thickness or density of the semi-reflective layer. For example, a mask can be placed between the deposition source and the substrate such that the thickness of deposited semi-reflective layer varies from a first location to a second location on an upper surface. The differential permeability and/or creation of a pattern on and within the semi-reflective layer can also be produced by post-treatment of the semi-reflective layer with localized energy inputs such as laser treatment to change the microstructure of the semi-reflective layer.

Any of the above-mentioned methods may be used to create one or more patterns on the semi-reflective layer. The choice of a given pattern or patterns may depend on a number of factors including, but not limited to, the analyte or analytes of interest, the semi-reflective material or materials used, the message, if any, displayed to a user, or a combination thereof.

Exemplary multi-layered films of the present invention having a substantially continuous semi-reflective layer are shown in U.S. Pat. No. 7,449,146 (Rakow et al.) FIGS. 1-3. In one exemplary multi-layered film sensor of the present invention, the multi-layered film sensor comprises a substantially continuous semi-reflective layer over a detection layer, wherein the detection layer has an increased surface area for potentially enhanced detection of an analyte due the presence of one or more wells within the detection layer (see U.S. '146, FIG. 3). Desirably, the substantially continuous semi-reflective layer positioned over the detection layer containing wells is a single layer of semi-reflective material.

In a further exemplary embodiment of the present invention, the semi-reflective layer is a discontinuous layer. In this embodiment, the composition of the semi-reflective layer may be substantially consistent across the semi-reflective layer; however, areas separate the semi-reflective layer into two or more discontinuous regions. The discontinuous semi-reflective layer may comprise any pattern of semi-reflective islands within a "sea" of exposed areas (i.e., the detection layer is exposed). The size and density of semi-reflective islands on the detection layer may vary as desired, and may be uniformly dispersed or non-uniformly dispersed over an upper surface of the detection layer. Typically, the semi-reflective islands are uniformly dispersed over an upper surface of the detection layer and have at least one dimension (i.e., length, width, or diameter) of at least about 1.0 micron ($\mu$m), desirably, from about 10.0 to about 100 $\mu$m; however, any semi-reflective island size, shape, and density may be used in the present invention. Further, the exposed areas typically have at least one dimension (i.e., length, width, or diameter) ranging from about 1.0 to about 100 $\mu$m; however, the exposed areas may have any dimensions in the present invention.

An exemplary multi-layered film of the present invention having a discontinuous semi-reflective layer is shown in FIG. 4 of U.S. Pat. No. 7,449,146 (Rakow et al.), incorporated herein by reference.

One suitable method for providing a discontinuous semi-reflective layer over a detection layer comprises laser ablation method as described in Example 11 of U.S. Pat. No. 7,449,146 (Rakow et al.). Portions of the semi-reflective layer may be removed by exposing the portions to a laser as described in U.S. Pat. Nos. 6,180,318 and 6,396,616 assigned to 3M Innovative Properties Company (St. Paul, Minn.), the subject of which is hereby incorporated in its entirety. Another exemplary method that could be used to produce a discontinuous semi-reflective layer is a photoimaging method.

In one desired embodiment, the discontinuous semi-reflective layer comprises a number of semi-reflective islands uniformly dispersed over an upper surface of the detection layer, wherein each semi-reflective island has an upper surface area in the shape of a square or circle having a length, width, or diameter of at least about 1.0 $\mu$m, more desirably, from about 10.0 to about 100 $\mu$m. It should be understood that each semi-reflective island may have an upper surface area in a variety of shapes including, but not limited to, triangular, rectangular, star-shaped, diamond-shaped, etc., and one or more dimensions of at least about 1.0 $\mu$m, more desirably, from about 10.0 to about 100 $\mu$m. Further, it should be understood that each semi-reflective island may be either permeable or impermeable to one or more analytes. When the semi-reflective islands are permeable to one or more analytes, the colorimetric sensor allows one or more analytes to contact the detection layer directly through exposed areas, as well as indirectly through the semi-reflective islands.

It should be noted that a laser ablation method (such as described in U.S. Pat. Nos. 6,180,318 and 6,396,616), a chemical etching method, or another method could be used to remove portions of the semi-reflective layer, as well as portions of the detection layer to form wells that extend from an upper surface of the semi-reflective layer into the detection layer, and possibly to an upper surface of the reflective layer (or an upper surface of the optional substrate). In this embodiment, the resulting structure comprises an array of multi-layered film islands (e.g., square islands having 100 $\mu$m sides within a grid of exposed areas having a width of about 10 $\mu$m) having the same detection layer composition and semi-reflective layer composition. The semi-reflective layer each island can be either permeable or impermeable to one or more analytes. When the semi-reflective islands are permeable to one or more analytes, the multilayer structures enable penetration of an analyte into the detection layer from the sides of the detection layer, as well as from the top of the detection layer. The size, shape and density of multi-layered film islands within the resulting structure may vary similarly to the semi-reflective islands described above. Typically, each multi-layered film island has one or more dimensions of at least about 1 $\mu$m such as about 10.0 to about 100 $\mu$m.

In addition to the above-described methods, multi-layered film islands may also be formed by depositing islands of detection layer material onto a reflective layer and then depositing a semi-reflective layer on top of each detection layer island. Various printing techniques including, but not limited to, ink jet printing and contact printing, may be used to deposit the detection layer in island or patterned form onto a reflective layer.

In one desired embodiment, the discontinuous semi-reflective layer comprises a single layer of semi-reflective islands over an upper surface of a detection layer, wherein the detection layer comprises at least one inorganic component. In a further desired embodiment, the discontinuous semi-reflective layer comprises a single layer of semi-reflective islands over an upper surface of a detection layer, wherein the detection layer comprises at least one inorganic component in combination with at least one polymer component. In yet a further desired embodiment, the discontinuous semi-reflective layer comprises a single layer of semi-reflective islands over an upper surface of a detection layer, wherein the detection layer comprises at least two different polymeric components, wherein the polymeric components are (1) blended with one another, (2) within a given layer but not blended with one another, (3) in a layer separate from one another, or (4) any combination of (1) to (3).

Detection Layer

The detection layer mixture may be homogeneous or heterogeneous, and may, for example, be made from a mixture of inorganic components, a mixture of organic components, or a mixture of inorganic and organic components. Detection layers made from a mixture of components may provide improved detection of analyte groups. The detection layer desirably has a range of pore sizes or a surface area selected to provide sorption characteristics like those of the sorbent media. Suitable porosity can be obtained using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, for example, with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent and porous layers of appropriate thickness for producing color or a colorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness and compatibility with wet etching treatments.

Representative porous silica materials are described in Ogawa et al., Chem. Commun. pp. 1149-1150 (1996), in Kresge et al., Nature, Vol. 359, pp. 710-712 (1992), in Jia et al., Chemistry Letters, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, Adv. Mater. 1998, Vol. 10, p. 313 (1998).

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. U.S. Pat. No. 7,449,146 (Rakow et al) contains an extensive list of such monomers. The above-mentioned polymers having intrinsic microporosity (PIMs) provide particularly desirable detection layers. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., Chem. Commun., 2004, pp. 230-231. Additional PIMs are disclosed in Budd et al., J. Mater. Chem., 2005, 15, pp. 1977-1986, in McKeown et al., Chem. Eur. J. 2005, 11, No. 9, 2610-2620 and in U.S. Pat. No. 7,690,514 (McKeown et al.), incorporated herein by reference.

The detection layer may comprise a pattern so as to create colored images, words, or messages upon exposure to an analyte. A sublayer may be patterned by having one or more portions that are reactive to a particular analyte and one or more portions that are non-reactive to the same analyte. Alternatively, a pattern of reactive material may be deposited on a larger non-reactive sublayer. In this case, it is preferable to make the patterned layer very thin so that no difference in optical thickness is apparent until an analyte is absorbed. The patterning can provide easily identifiable warnings for a user upon exposure to an analyte.

In most embodiments, the detection layer comprises at least one PIM whose optical thickness changes upon exposure to an analyte. The change in optical thickness can be caused by a dimensional change such as a change in physical thickness of the polymer due to swelling or shrinkage or a change in refractive index of the detection layer due to the presence or chemical reaction of the analyte. The detection layer may change from one color to another, from a color to no color, or from no color to a color.

The thickness of the detection layer may be patterned, for example, as described in U.S. Pat. No. 6,010,751. This may be desirable when the sensor is designed so that the presence of an analyte causes the detection layer to swell or shrink, thereby making a pattern disappear (for example when a thinner portion swells to the same thickness as a thicker portion) or appear (for example, when an portion shrinks to a thinner thickness than an adjacent portion). Patterns may also be made to appear by starting with thinner and thicker regions that appear the same color initially, but, when exposed to one or more analytes, one or both of the thinner and thicker regions swell to give two different hues.

Reflective Layer

The reflective layer may comprise any material that can form a fully reflective or semi-reflective layer. It is preferable that the material is fully reflective at a thickness of about 20 to about 200 nm. Thinner layers can typically be used to make the reflective layer semi-reflective. Although the reflective layer is typically made to be more reflective than the semi-reflective layer, sometimes it is desirable to have the reflectivity of the reflective layer and semi-reflective layer be the same so a response to the presence of an analyte can be seen from either side of the sensor film. The reflective layer is permeable to the analyte.

Suitable materials for the reflective layer include metals or semi-metals such as aluminum, chromium, gold, nickel, silicon, and silver. Other suitable materials that may be included in the reflective layer include metal oxides such as chromium oxide and titanium oxide.

In some exemplary embodiments of the present invention, the reflective layer is at least about 90% reflective (i.e., at least about 10% transmissive), and in some embodiments, about 99% reflective (i.e., about 1% transmissive). In other exemplary embodiments of the present invention, the reflective layer is a semi-reflective layer, wherein the reflective layer is at least about 20% reflective, such as about 20 to about 90% reflective, or about 30 to about 70% reflective.

In some embodiments, the reflective layer also acts as the substrate, providing support for the sensor. The reflective layer may be a substantially continuous layer or a discontinuous layer. Further, the reflective layer may comprise one or more reflective layers. Desirably, the reflective layer comprises a single reflective layer.

Masking Layer

The sensor further comprises a masking layer that comprises (with reference to FIG. 1) an adhesive masking layer 57 and optional masking film 54 affixed to the surface of the reflective layer 52, said adhesive masking layer comprising an adhesive (meth)acryloyl copolymer having a $T_g$ of $\geq 0°$ C., and comprising a) high $T_g$ monomer units and b) alkyl (meth)acryloyl monomer units.

The masking layer may be provided over the semi-reflective layer in the form of a pattern. In this embodiment, upon exposure to an analyte, the sensor displays a signal in the form of a pattern (i.e., a reverse pattern of the masking layer on the semi-reflective layer). The signal pattern may have any desired configuration including, but not limited to, shapes, letters, words, a specific message to the user, safety instructions to the user, a company logo, etc.

The optional, yet preferable masking film comprises a polymeric film that is impermeable to the analytes such as chemical agents. Suitable materials for polymeric film of the masking layer include polyolefins, polystyrene, polyester, polyvinyl chloride, polyvinyl alcohol, polyurethane, poly(vinylidene fluoride), cellulose and cellulose derivates. Such films are generally laminated The (meth)acryloyl adhesive copolymer of masking layer 57 comprise at least one high $T_g$ monomer. The adhesive may be described as interpolymerized reaction product of: (a) at least one high Tg monomer; (b) at least one alkyl (meth)acryloyl acid ester monomer, optionally (c) at least one acid functional monomer, optionally (d) at least one non-acid-functional polar monomer, optionally (e) at least one vinyl monomer, and optionally (f) at least one multi-functional (meth)acrylate monomer.

As used herein the term "(meth)acrylic" or "(meth)acryloyl" is inclusive of both acrylic and methacrylic (or acryloyl and methacryloyl) and is inclusive of (meth)acrylamides. The copolymer has a Tg of $\geq 0°$ C., preferably $\geq 10°$ C., more preferably $\geq 20°$ C.

A useful predictor of interpolymer $T_g$ for specific combinations of various monomers can be computed by application of Fox Equation: $1/Tg = \Sigma Wi/Tgi$. In this equation, Tg is the glass transition temperature of the mixture, Wi is the weight fraction of component i in the mixture, and Tgi is the glass transition temperature of component i, and all glass transition temperatures are in Kelvin (K). Alternatively, the glass transition temperature can be measured in a variety of known ways, including, e.g., through differential scanning calorimetry (DSC). As used herein the term "high Tg monomer" refers to a monomer, which when homopolymerized, produce a (meth)acryloyl copolymer having a Tg of $\geq 0°$ C. The incorporation of the high Tg monomer to the adhesive (meth)acryloyl copolymer is sufficient to raise the glass transition temperature of the resulting copolymeric adhesive to $\geq 0°$ C., preferably $\geq 10°$ C., more preferably $\geq 20°$ C., as calculated using the Fox Equation. Alternatively the (meth)acryloyl copolymeric adhesives may be prepared and the Tg measured by DSC.

According to Donatas Satas, *Handbook of Pressure Sensitive Adhesives*, 1st Edition, Von Nostrand Rheinhold, N.Y., 1982: "the glass transition temperature is neither an accurate measurement of polymer stiffness at room temperature, nor is it an accurate measure of pressure sensitive properties. It is an easy and convenient method to predict the suitability of a polymer for pressure-sensitive adhesive application and to predict the effect of a comonomer on the copolymer properties."

High Tg monomers are those that may be co-polymerized with (meth)acrylic monomers and have a Tg of $\geq 0°$ C., preferably $\geq 10°$ C., more preferably $\geq 20°$ C. (as estimated by the Fox Equation using the homopolymer). High Tg monomer units are selected from t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, biphenyl methacrylate and propyl methacrylate, halogenated aryl acrylates, acrylamide, N,N-dimethylacrylamide, N-methylacrylamide, N-isopropylacrylamide, N-tert-butylacrylamide, N-phenylacrylamide, N-(1,1-dimethyl-3-oxobutyl)acrylamide, N-vinyl pyrrolidone, hexadecyl acrylate, methacrylic acid, acrylic acid, glycidyl methacrylate, 2-hydroxyethyl methacrylate, 2-hydroxypropyl methacrylate, stearyl acrylate, 2-phenoxyethyl methacrylate, trimethylsilyl methacrylate, 3,3,5-trimethylcyclohexyl methacrylate, and combinations thereof.

Preferably high Tg monomers include aryl (meth)acryloyl monomers including phenyl, biphenyl, fluorene, isobornyl (meth)acrylate, N,N-dimethyl acrylamide, (meth)acrylic acid, and methyl methacrylate.

An alkyl (meth)acryloyl monomer useful in preparing the (meth)acryloyl copolymer is a monomeric (meth)acrylic acid ester of a non-tertiary alcohol, which alcohol contains from 1 to 14 carbon atoms and preferably an average of from 4 to 12 carbon atoms.

Examples of monomers suitable for use as the (meth)acrylate ester monomer include an esters of either acrylic acid or methacrylic acid with a non-tertiary alcohol such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable sources, such as 2-octanol, citronellol or dihydrocitronellol. In some embodiments the corresponding (meth)acrlamides may be used.

The (meth)acryloyl adhesive copolymer optionally includes an acid-functional ethylenically unsaturated monomer, where the acid-functional group may be an acid per se, such as a carboxylic acid, or a portion may be salt thereof, such as an alkali metal carboxylate. Useful acid-functional ethylenically unsaturated monomers include, but are not limited to, those selected from an ethylenically unsaturated carboxylic acid, ethylenically unsaturated sulfonic acid, ethylenically unsaturated phosphonic acid, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid-functional ethylenically unsaturated monomers of the acid- and epoxy-functional (meth)acrylic copolymer are generally selected from ethylenically unsaturated carboxylic acids, i.e., (meth)acrylic acids. When an even stronger acid is desired, an acid-functional ethylenically unsaturated monomer includes an ethylenically unsaturated sulfonic acid, an ethylenically unsaturated phosphonic acid, or a mixture thereof.

The optional acid-functional ethylenically unsaturated monomer may be used in an amount of at least 1 part by weight, based on 100 parts by weight of the total monomer content that would form an unmodified acid-functional (meth)acrylic copolymer. In certain embodiments, 1 part to 40 parts by weight acid-functional ethylenically unsaturated monomer is used, based on 100 parts by weight of the total monomer content that would form an unmodified acid-functional (meth)acrylic copolymer.

In certain embodiments, a non-acid-functional polar monomer is used in making the (meth)acryloyl adhesive copolymer. As used herein, the term "polar monomer" is exclusive of an acid-functional ethylenically unsaturated monomer, and is referred to as a "non-acid-functional polar monomer."

Representative examples of a suitable non-acid-functional polar monomer includes, but is not limited to, 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth) acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of acrylamide, 2-hydroxyethyl (meth)acrylate and N-vinylpyrrolidinone.

A non-acid-functional polar monomer may be used in an amount of 0 to 10 parts by weight, based on 100 parts by weight of the total monomer. In certain embodiments, such monomer is used in an amount of at least 0.5 part by weight of the 100 parts of the total monomer. In certain embodiments, such monomer is used in an amount of no greater than 5 parts by weight of the 100 parts of the total monomer.

When used, vinyl monomers useful in the (meth)acryloyl adhesive copolymer include a vinyl ester (e.g., vinyl acetate and vinyl propionate), styrene, substituted styrene (e.g., α-methyl styrene), vinyl halide, and mixtures thereof. As used herein, the term "vinyl monomer" is exclusive of an acid-functional ethylenically unsaturated monomer, an acrylate ester monomer, and a polar monomer.

A vinyl monomer may be used in an amount of 0 to 5 parts by weight, based on 100 parts by weight of the total monomer content that would form an unmodified acid-functional (meth)acrylic copolymer. In certain embodiments, such monomer is used in an amount of at least 1 part by weight of the 100 parts of the total monomer content that would form an unmodified acid-functional (meth)acrylic copolymer.

In order to increase cohesive strength of the coated adhesive composition, a multifunctional (meth)acrylate monomer may be incorporated into the blend of polymerizable monomers to assist in crosslinking. Such compounds are often referred to as chemical crosslinking agents. A multifunctional (meth)acrylate is particularly useful for emulsion or syrup polymerization. Examples of useful multifunctional (meth)acrylates include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition.

If used, typically, a multifunctional (meth)acrylate is used in an amount of less than 5 parts by weight, relative to 100 parts by weight of the total monomer content that would form an unmodified acid-functional (meth)acrylic copolymer. In certain embodiments, a multifunctional (meth)acrylate crosslinker may be present in an amount of less than 1 part by weight. In certain embodiments, such chemical crosslinker is used in an amount of at least 0.01 part by weight. In certain embodiments, such chemical crosslinker is used in an amount of at least 0.05 part by weight. In some embodiments the crosslinking compositions contain no multifunctional (meth)acrylates.

With respect to each of the acid-functional monomers, polar monomers and vinyl monomers, each may be considered a high Tg monomer if the Tg of the homopolymer is greater than or equal to 0° C.

A (meth)acryloyl adhesive copolymer can be prepared by a conventional free radical polymerization method, including solution, radiation, bulk, dispersion, emulsion, and suspension processes. For example, it may be prepared via suspension polymerizations as disclosed in U.S. Pat. No. 3,691,140 (Silver); U.S. Pat. No. 4,166,152 (Baker et al.); U.S. Pat. No. 4,636,432 (Shibano et al.); U.S. Pat. No. 4,656,218 (Kinoshita); and U.S. Pat. No. 5,045,569 (Delgado). Each describes adhesive compositions, and the descriptions of polymerization processes.

The (meth)acryloyl copolymer adhesives described herein are low outgassing. Many acrylic based adhesives have high levels of residual solvent and/or monomer that will migrate into the sensor, resulting in an undesired color change.

For any (meth)acryloyl adhesive copolymer, the nature and amount of each monomer; a) the high Tg monomer, b) the (meth)acrylate monomer, c) the acid-functional monomer, d) the non-acid polar monomer, e) the other vinyl monomers, and f) the multifunctional(meth)acrylate crosslinker, are chosen such that the resultant copolymer have a Tg≥0° C., preferably ≥10° C., more preferably ≥20° C., as calculated using the Fox Equation or as measured by DSC.

As an Example, selecting isooctyl acrylate as the acrylic ester monomer, one would have to select a high Tg monomer in the amounts listed in the following Table to achieve the desired Tg of the copolymer, as calculated by the Fox Equation:

| Tg of high Tg monomer | Wt. % to reach 0° C. | Wt. % to reach 5° C. | Wt. % to reach 10° C. | Wt. % to reach 15° C. | Wt. % to reach 25° C. |
|---|---|---|---|---|---|
| 10 | 88 | 94 | 100 | — | — |
| 20 | 80 | 85 | 90 | 95 | — |
| 30 | 73 | 78 | 83 | 87 | 95 |
| 40 | 68 | 72 | 77 | 81 | 89 |
| 50 | 64 | 68 | 72 | 76 | 83 |
| 60 | 60 | 64 | 68 | 71 | 79 |
| 70 | 57 | 61 | 64 | 68 | 75 |
| 80 | 54 | 58 | 61 | 65 | 71 |
| 90 | 52 | 56 | 59 | 62 | 68 |
| 100 | 50 | 53 | 56 | 60 | 66 |

Further information regarding the Fox Equation may be obtained from W. R. Sorenson and T. W. Campbell's text entitled "Preparative Methods of Polymer Chemistry", Interscience: New York (1968), p. 209). Specific values for $T_g$s of appropriate homopolymers can be obtained from P. Peyser's chapter in "Polymer Handbook", 3rd edition, edited by J. Brandrup and E. H. Immergut, Wiley: New York (1989), pp. VI-209 through VI-277.

The above-described compositions may be coated on either the masking film or the reflective layer using conventional coating techniques modified as appropriate to the particular substrate. For example, these compositions can be applied to a variety of solid substrates by methods such as roller coating, flow coating, dip coating, spin coating, spray coating knife coating, and die coating. These various methods of coating allow the compositions to be placed on the substrate at variable thicknesses thus allowing a wider range of use of the compositions. Coating thicknesses may vary, but coating thicknesses of 2-500 microns (dry thickness), preferably about 25 to 250 microns, are contemplated. In some embodiments the adhesives may be coated from the melt.

In one embodiment, the pressure-sensitive adhesives are applied to the film body in the form of pressure-sensitive tapes, wherein they are coated on a liner film, cut into pieces, and then adhered to the sensor film. In this implementation, the liner often provides polymer film layer 54 of the masking layer. The polymer film layer also provides an additional barrier to permeation of vapors into the sensor. In a similar fashion, a backing may be used, thus providing a masking tape, which may be adhesively affixed to reflective layer 52 thereby providing elements 57 and 54.

The instant sensors may be used as "end of service life indicators" (ESLIs) for users of disposable personal respirators, powered air purifying respirators, haz-mat suits and other protective devices of the presence of undesired materials. For example, an end-of-service-life indicator ("ESLI") can warn that a filter element in such a device may be approaching saturation or may be ineffective against a particular material.

The instant sensors, when used as ESLIs may be used in filter cartridges to assist in informing the user of when the cartridge has met the end of its service life. The filter cartridges may comprise a housing, filter media disposed within the housing, and the instant sensor visible through a sidewall of the housing. A respirator incorporating the instant ESLIs may comprise a mask body, a harness that is secured to the mask body, and one or more filter cartridges attachable to the mask body.

The ESLIs may be disposed adjacent to the housing sidewall so that they can be easily viewed from the exterior. The ESLIs are generally designed to be colorimetric sensors—that is they change visually after being exposed to a sufficient amount of contaminant in the filtered air. The color change and sensor placement are tailored to provide indication that coincides with when the filter cartridge service life ends. The instant sensors advantageously provide improved contrast of exposed and non-exposed (masked) regions when view from acute angles. Further details regarding filter cartridge and respirator construction may be found in Applicant's copending application U.S. Ser. No. 12/604,565, filed 23 Oct. 2009, and incorporated herein by reference.

The disclosed sensors may be used to detect a variety of vapors of interest. Representative vapors of interest include water vapor, gases, and volatile organic chemical compounds. Representative organic chemical compounds include substituted or unsubstituted carbon compounds including alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile.

EXAMPLES

Materials and Suppliers

Polyisobutylenes: Oppanol® B150 ($M_w$—2,500,000 g/mol); BASF Corp.; Florham Park, N.J.).
Solvents: Methanol, ethyl acetate, and toluene—EMD Chemical Inc.; Gibbstown N.J.
Acrylic monomers: IOA, IBOA, EA, nBA, MA, AA—Sigma Aldrich; St. Louis Mo.
Polymerization initiator: Vazo® 67; DuPont; Wilmington Del.
Release liner: (T10)—Clearsil® T10 silicone coated release liners; CP Films, Inc.; Martinsville Va.
PET liner: (3SAB)—Hostaphan® 3SAB silicone coated polyester film—0.051 millimeter thick; Mitsubishi Polyester Film, Inc.; Greer S.C.

Example 1

An 8 ounce, narrow-mouthed amber bottle with Teflon®-wrapped threads was charged with 16.5 g of isobornyl acrylate (IBOA), 12.0 g of isooctyl acrylate (IOA), 1.5 g of acrylic acid (AA) and 70.0 g of ethyl acetate. Then 0.030 g of polymerization initiator (Vazo® 67) was added and the mixture was sparged with nitrogen for 15 minutes. The bottle was sealed with a Teflon®-lined metal cap, and further sealed with Teflon® tape and electrical tape. The bottle was placed in a water bath at 65° C. and gently tumbled. After 18 hours, the bottle was removed from the water bath and allowed to cool to room temperature. The resulting adhesive polymer composition had about 30 weight percent solids, and an IBOA/IOA/AA composition of about 55/40/5.

The glass transition temperature ($T_g$) of the polymer was calculated to be 13° C. The $T_g$ was calculated using the Fox Equation: $1/T_g = \Sigma_i (W_i/T_{gi})$, wherein $T_g$ is the glass transition temperature of the copolymer, W, is the weight fraction of monomer i, and $T_{gi}$ is the glass transition temperature of a homopolymer of monomer i.

The adhesive composition was knife coated onto a PET liner (3SAB) and the coated liner was taped to a thin aluminum panel. The coated adhesive was dried in an oven set at 70° C. for 20 minutes followed by drying in an oven set at 120° C. for 30 minutes. The adhesive was allowed to cool to room temperature. The resulting adhesive film had a thickness of about 0.051 mm, and a release liner (T10) was laminated to it. Samples measuring about 2.5 cm square were cut from the adhesive sheet for testing.

A multilayered sensor film for an ESLI was prepared according to the procedure described in the example of U.S. patent application Ser. No. 12/604,565 filed on Oct. 23, 2009, incorporated herein by reference.

The adhesive square was heated gently with a heat gun for about 10 seconds, and then laminated to the back side (silvered side) of the sensor film using a cotton-tipped applicator. Acrylate adhesives with a calculated $T_g$ greater than 0° C. were heated gently with a heat gun for about 10 seconds before bonding to the sensor film.

The visual appearance of the sensor film was observed at the time intervals shown in Table 1 and the visual change in appearance was recorded. The films were maintained at ambient temperature (about 21° C.). The change in appearance, often described as a subtle change in hue at oblique viewing angles, was assigned a value from 0-5 with 0 indicating no observable change and 5 being a very obvious visual change.

Examples 2-25

Adhesives were prepared and tested on ESLI sensor films according to the procedure described in Example 1 except as follows.

Adhesives for Examples 2-25 were prepared using the monomers shown in Table 1. Examples 2, 7, 9, 11, 13, and 15 included 1% by weight of the aziridine crosslinking agent prepared according to Preparative Example 1 of U.S. 2010/0227969.

Adhesives for Examples 16-25 were prepared with only IOA and IBOA.

Adhesives from Examples 1, 3, 4, and 5 were also tested after aging for 24 and 72 hours at 50° C. and at 80° C., respectively.

Example C1-C3

C1 was a polyisobutylene adhesive prepared by dissolving about 10% by weight of a polyisobutylene (Oppanol® B150) in toluene and coating on a PET liner.

C2 was an acrylate adhesive prepared according the procedure of Example 1 with IOA, EA (ethyl acrylate) and AA and a ratio of 50:40:10, and coated on a PET liner.

C3 was an acrylate adhesive prepared according the procedure of Example 1 with BA (butyl acrylate), MA (methyl acrylate), and AA in a ratio of 58:40:2 and coated on a PET liner.

The adhesive-coated PET liners were taped to thin aluminum panels and dried in an oven set at 70° C. for 20 minutes followed by placing in an oven set at 120° C. for an additional 30 minutes. The adhesives were prepared with a dry thickness of about 2 mils (0.051 mm) and tested according the procedure of Example 1 on ESLI sensor films. Results are shown in Table 1.

TABLE 1

| | Composition | | | Tg | Visual Change | | | | | 50° C. | 80° C. |
|---|---|---|---|---|---|---|---|---|---|---|---|
| Ex | IOA | IBOA | AA | ° C. | 5 min | 10 min | 15 min | 30 min | 72 h | 24 h | 72 h |
| 1 | 40 | 55 | 5 | 13 | 0 | 0 | 0 | 0 | 0 | 0 | 1 |
| 2 | 40 | 55 | 5 | 13 | 0 | 0 | 0 | 0 | 0 | NT | NT |
| 3 | 45 | 50 | 5 | 6 | 0 | 0 | 0 | 0 | 0 | 0 | 1 |
| 4 | 50 | 45 | 5 | −2 | 0 | 0 | 0 | 0 | 0 | 0 | 1 |
| 5 | 55 | 40 | 5 | −8 | 0 | 0 | 0 | 0 | 1 | 0 | 1 |
| 6 | 35 | 60 | 5 | 22 | 0 | 0 | 0 | 0 | 0 | NT | NT |
| 7 | 35 | 60 | 5 | 22 | 0 | 0 | 0 | 0 | 0.5 | NT | NT |
| 8 | 30 | 65 | 5 | 30 | 0 | 0 | 0 | 0 | 0 | NT | NT |
| 9 | 30 | 65 | 5 | 30 | 0 | 0 | 0 | 0 | 0 | NT | NT |
| 10 | 25 | 75 | 5 | 39 | 0 | 0 | 0 | 0 | 0 | NT | NT |
| 11 | 25 | 75 | 5 | 39 | 0 | 0 | 0 | 0 | 0 | NT | NT |
| 12 | 20 | 70 | 5 | 49 | 0 | 0 | 0 | 0 | 0.5 | NT | NT |
| 13 | 20 | 70 | 5 | 49 | 0 | 0 | 0 | 0 | 0.5 | NT | NT |
| 14 | 15 | 80 | 5 | 59 | 0 | 0 | 0 | 0 | 1 | NT | NT |
| 15 | 15 | 80 | 5 | 59 | 0 | 0 | 0 | 0 | 1 | NT | NT |
| 16 | 70 | 30 | 0 | −27 | 1 | 2 | 2 | 2 | 3 | NT | NT |
| 17 | 65 | 35 | 0 | −22 | 1 | 2 | 2 | 2 | 3 | NT | NT |
| 18 | 55 | 45 | 0 | −9 | 0 | 0 | 0 | 1 | 3 | NT | NT |
| 19 | 50 | 50 | 0 | −2 | 0 | 0 | 0 | 1 | 3 | NT | NT |
| 20 | 45 | 55 | 0 | 5 | 0 | 0 | 0 | 0 | 0 | NT | NT |
| 21 | 40 | 60 | 0 | 13 | 0 | 0 | 0 | 0 | 0 | NT | NT |
| 22 | 35 | 65 | 0 | 21 | 0 | 0 | 0 | 0 | 0 | NT | NT |
| 23 | 25 | 75 | 0 | 39 | 0 | 0 | 0 | 0 | 1 | NT | NT |
| 24 | 20 | 80 | 0 | 49 | 0 | 0 | 0 | 0 | 1 | NT | NT |
| 25 | 15 | 85 | 0 | 59 | 0 | 0 | 0 | 0 | 1 | NT | NT |
| C1 | Polyisobutylene | | | −62 | 1 | 2 | 3 | 3 | 4 | NT | NT |
| C2 | IOA:EA:AA | | | −35 | 0 | 0 | 1 | 2 | 3 | NT | NT |
| C4 | BA:MA:AA | | | −30 | 0 | 0 | 1 | 2 | 4 | NT | NT |

NT—Not tested

Examples 26-36

Adhesives were prepared, coated, and tested on ESLI sensor films according to the procedure described in Example 1 and using the monomer compositions shown in Table 2. Adhesives for Examples 30 and 35 included 1% by weight of the aziridine crosslinker of Example 2. Results after 72 hours are shown in Table 2. Adhesives from Examples 26, 27, 28, and 31 were also tested after 24 hours at 50° C. and 72 hours at 80° C.

TABLE 2

| | Composition | | | | | Visual Change | | |
|---|---|---|---|---|---|---|---|---|
| | | | | | | | 24 h | 72 h |
| Ex | nBA | IBOA | AA | $T_g$ (° C.) | 72 h | | 50° C. | 80° C. |
| 26 | 55 | 40 | 5 | −5 | 0 | | 0 | 1 |
| 27 | 50 | 45 | 5 | 2 | 0 | | 0 | 1 |
| 28 | 45 | 50 | 5 | 9 | 0 | | 0 | 1 |
| 29 | 40 | 55 | 5 | 16 | 0 | | NT | NT |
| 30 | 40 | 55 | 5 | 16 | 0 | | NT | NT |
| 31 | 35 | 60 | 5 | 24 | 0 | | 0 | 0.5 |
| 32 | 35 | 65 | 0 | 24 | 0 | | NT | NT |
| 33 | 30 | 70 | 0 | 32 | 0 | | NT | NT |
| 34 | 70 | 0 | 30 | −22 | 1 | | NT | NT |

The invention is illustrated by the following embodiments:
1. A chemical sensor comprising:
   a) a multilayer body comprising:
      i) a semireflective layer;
      ii) a detection layer and that is responsive to the presence of a chemical agent by providing a visual change;
      iii) a reflective layer; and
   b) an adhesive masking layer affixed to the surface of the reflective layer, said adhesive masking layer having a $T_g$ of ≥0° C. comprising a (meth)acryloyl adhesive copolymer of a) high $T_g$ monomer units and b) alkyl (meth)acryloyl monomer units.
2. The chemical sensor of embodiment 1 wherein the adhesive masking layer comprises an (meth)acryloyl adhesive copolymer layer and a film layer.

3. The sensor of any of the previous embodiments, wherein said (meth)acryloyl adhesive copolymer further comprises c) acid functional monomer units.

4. The sensor of any of the previous embodiments, wherein said high $T_g$ monomer units of said (meth)acryloyl adhesive copolymer are selected from t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, biphenyl methacrylate, propyl methacrylate, halogenated phenyl acrylates, acrylamide, N,N-dimethylacrylamide, N-methylacrylamide, N-isopropylacrylamide, N-tert-butylacrylamide, N-phenylacrylamide, N-(1,1-dimethyl-3-oxobutyl)acrylamide N-vinyl pyrrolidone, hexadecyl acrylate, methacrylic acid, acrylic acid, glycidyl methacrylate, 2-hydroxyethyl methacrylate, 2-hydroxypropyl methacrylate, stearyl acrylate, 2-phenoxyethyl methacrylate, trimethylsilyl methacrylate, and 3,3,5-trimethylcyclohexyl methacrylate or combinations thereof 5. The sensor of any of the previous embodiments wherein said (meth)acryloyl adhesive copolymer comprises:
 a) 5 to 95 parts by weight of said high Tg monomer units;
 b) 95 to 55 parts by weight of said alkyl (meth)acryloyl monomer units;
 c) 0 to 40 parts by weight of acid functional monomer units;
 d) 0 to 15 parts by weight of polar monomers;
 e) 0 to 5 parts by weight of other vinyl monomers, and
 f) 0 to 5 parts by weight of multifunctional (meth)acrylates;
  wherein the sum of the monomers is 100 parts by weight; and optionally a plasticizer.

6. The sensor of any of the previous embodiments wherein said (meth)acryloyl adhesive copolymer comprises:
 a) at least 88 wt. % of said high Tg monomer units having a Tg of 10° C.;
 b) at least 80 wt. % of said high Tg monomer units having a Tg of 20° C.;
 c) at least 73 wt. % of said high Tg monomer units having a Tg of 30° C.;
 d) at least 68 wt. % of said high Tg monomer units having a Tg of 40° C.;
 e) at least 64 wt. % of said high Tg monomer units having a Tg of 50° C.;
 f) at least 60 wt. % of said high Tg monomer units having a Tg of 60° C.;
 g) at least 57 wt. % of said high Tg monomer units having a Tg of 70° C.;
 h) at least 54 wt. % of said high Tg monomer units having a Tg of 80° C.;
 i) at least 52 wt. % of said high Tg monomer units having a Tg of 90° C.; or
 j) at least 50 wt. % of said high Tg monomer units having a Tg of 100° C.

7. The sensor of any of the previous embodiments wherein said (meth)acryloyl adhesive copolymer has a Tg of ≥5° C.

8. The sensor of any of the previous embodiments wherein said (meth)acryloyl adhesive copolymer has a Tg of ≥10° C.

9. The sensor of any of the previous embodiments wherein the detection layer comprises polymers having intrinsic microporosity (PIMs).

10. The sensor of any of the previous embodiments, wherein said copolymer further comprises a multifunctional (meth)acrylate crosslinker.

11. The sensor of any of the previous embodiments wherein the sensor detects organic vapors.

12. A filter cartridge that comprises a housing, filter media disposed within the housing, and the sensor of any of the previous embodiments visible through a sidewall of the housing.

13. The filter cartridge of embodiment 12, wherein the filter cartridge comprises one or more markings that indicate filter cartridge remaining life.

14. The filter cartridge of embodiment 13, wherein the marking(s) are molded into the sidewall of the cartridge housing.

15. A respirator that comprises a mask body and one or more filter cartridges of embodiments 12-14.

16. A respirator that comprises a mask body, a harness that is secured to the mask body, and one or more cartridges of embodiment 15 attachable to the mask body.

What is claimed is:
1. A chemical sensor comprising:
 a) a multilayer body comprising:
  i) a semireflective layer;
  ii) a detection layer and that is responsive to the presence of a chemical agent by providing a visual change;
  iii) a reflective layer; and
 b) an adhesive masking layer affixed to the surface of the reflective layer, said adhesive masking layer comprising a (meth)acryloyl adhesive copolymer having a $T_g$ of ≥0° C. comprising a) high $T_g$ monomer units and b) alkyl (meth)acryloyl monomer units; and
  wherein the adhesive masking layer further comprises a film layer.

2. The sensor of claim 1, wherein said (meth)acryloyl adhesive copolymer further comprises c) acid functional monomer units.

3. The sensor of claim 1, wherein said high Tg monomer units of said (meth)acryloyl adhesive copolymer are selected from t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, biphenyl methacrylate, propyl methacrylate, halogenated phenyl acrylates, acrylamide, N,N-dimethylacrylamide, N-methylacrylamide, N-isopropylacrylamide, N-tert-butylacrylamide, N-phenylacrylamide, N-(1,1-dimethyl-3-oxobutyl)acrylamide N-vinyl pyrrolidone, hexadecyl acrylate, methacrylic acid, acrylic acid, glycidyl methacrylate, 2-hydroxyethyl methacrylate, 2-hydroxypropyl methacrylate, stearyl acrylate, 2-phenoxyethyl methacrylate, trimethylsilyl methacrylate, and 3,3,5-trimethylcyclohexyl methacrylate or combinations thereof.

4. The sensor of claim 1 wherein said (meth)acryloyl adhesive copolymer comprises:
 a) 5 to 95 parts by weight of said high $T_g$ monomer units;
 b) 95 to 55 parts by weight of said alkyl (meth)acryloyl monomer units;
 c) 0 to 40 parts by weight of acid functional monomer units;
 d) 0 to 15 parts by weight of polar monomers;
 e) 0 to 5 parts by weight of other vinyl monomers, and
 f) 0 to 5 parts by weight of multifunctional (meth)acrylates;
  wherein the sum of the monomers is 100 parts by weight; and
  optionally a plasticizer.

5. The sensor of claim 1 wherein said (meth)acryloyl adhesive copolymer comprises:
   a) at least 88 wt. % of said high $T_g$ monomer units having a $T_g$ of 10° C.;
   b) at least 80 wt. % of said high $T_g$ monomer units having a $T_g$ of 20° C.;
   c) at least 73 wt. % of said high $T_g$ monomer units having a $T_g$ of 30° C.;
   d) at least 68 wt. % of said high $T_g$ monomer units having a $T_g$ of 40° C.;
   e) at least 64 wt. % of said high $T_g$ monomer units having a $T_g$ of 50° C.;
   f) at least 60 wt. % of said high $T_g$ monomer units having a $T_g$ of 60° C.;
   g) at least 57 wt. % of said high $T_g$ monomer units having a $T_g$ of 70° C.;
   h) at least 54 wt. % of said high $T_g$ monomer units having a $T_g$ of 80° C.;
   i) at least 52 wt. % of said high $T_g$ monomer units having a $T_g$ of 90° C.; or
   j) at least 50 wt. % of said high $T_g$ monomer units having a $T_g$ of 100° C.

6. The sensor of claim 1 wherein said (meth)acryloyl adhesive copolymer has a $T_g$ of ≥5° C.

7. The sensor of claim 1 wherein said (meth)acryloyl adhesive copolymer has a $T_g$ of ≥10° C.

8. The sensor of claim 1 wherein the detection layer comprises polymers having intrinsic microporosity (PIMs).

9. The sensor of claim 1, wherein said copolymer further comprises a multifunctional (meth)acrylate crosslinker.

10. The sensor of claim 1 wherein the sensor detects organic vapors.

11. A filter cartridge that comprises a housing, filter media disposed within the housing, and the sensor of claim 1 visible through a sidewall of the housing.

12. The filter cartridge of claim 11, wherein the filter cartridge comprises one or more markings that indicate filter cartridge remaining life.

13. The filter cartridge of claim 12, wherein the marking(s) are molded into the sidewall of the cartridge housing.

14. A respirator that comprises a mask body and one or more filter cartridges of claim 11.

15. A respirator that comprises a mask body, a harness that is secured to the mask body, and one or more cartridges of claim 11 attachable to the mask body.

* * * * *

UNITED STATES PATENT AND TRADEMARK OFFICE
CERTIFICATE OF CORRECTION

PATENT NO.       : 9,442,073 B2  
APPLICATION NO.  : 13/980583  
DATED            : September 13, 2016  
INVENTOR(S)      : Guy Joly It is certified that error appears in the above-identified patent and that said Letters Patent is hereby corrected as shown below:

In the Specification

Column 16,  
Line 29, delete "W," and insert -- $W_i$ --, therefor.  
Line 30, delete "$T_g$," and insert -- $T_{gi}$ --, therefor.

Column 19,  
Line 22, after "thereof" insert -- . --.

Signed and Sealed this  
Third Day of January, 2017

Michelle K. Lee  
*Director of the United States Patent and Trademark Office*